United States Patent [19]

Boxhoorn

[11] Patent Number: 4,783,437

[45] Date of Patent: * Nov. 8, 1988

[54] SILVER-CONTAINING ETHYLENE OXIDE CATALYST AND A PROCESS FOR ITS PREPARATION

[75] Inventor: Gosse Boxhoorn, Amsterdam, Netherlands

[73] Assignee: Shell Oil Company, Houston, Tex.

[*] Notice: The portion of the term of this patent subsequent to Oct. 20, 2004 has been disclaimed.

[21] Appl. No.: 66,171

[22] Filed: Jun. 25, 1987

[30] Foreign Application Priority Data

Jul. 28, 1986 [GB] United Kingdom ............... 8618325

[51] Int. Cl.$^4$ ..................... B01J 21/04; B01J 23/04; B01J 23/14; B01J 23/50
[52] U.S. Cl. ................................. 502/348; 549/536
[58] Field of Search .......................... 502/347, 348

[56] References Cited

U.S. PATENT DOCUMENTS 4,242,235  12/1980  Cognion et al. ............... 502/348 X
4,575,494  3/1986  Young et al. ...................... 502/243

Primary Examiner—W. J. Shine

[57] ABSTRACT

The invention relates to a process for the preparation of a silver-containing catalyst suitable for the oxidation of ethylene to ethylene oxide which comprises
(a) mixing alumina with a tin compound and with an alkali metal compound,
(b) calcining the mixture to obtain an alkali-enriched and tin containing alumina carrier,
(c) applying a silver compound to the alumina carrier and converting said silver compound to metallic silver.

The catalyst has a high activity, a high selectivity combined with a very high stability.

19 Claims, No Drawings

SILVER-CONTAINING ETHYLENE OXIDE CATALYST AND A PROCESS FOR ITS PREPARATION

FIELD OF THE INVENTION

The invention relates to a process for the preparation of a silver-containing catalyst, suitable for the preparation of ethylene oxide, to the prepared catalyst and to the use of the catalyst for the preparation of ethylene oxide.

BACKGROUND OF THE INVENTION

It is generally known for a silver-containing catalyst to be employed in the preparation of ethylene oxide. See for example U.S. Pat. No. 3,962,136 and also the literature cited therein. In order to obtain improved silver catalysts, efforts have been directed for many years towards modifying the silver catalysts with the aid of promoters. For example, the above-mentioned U.S. Pat. No. 3,962,136 describes a process in which a silver compound is applied to a carrier, after which the applied silver compound is reduced to silver and in which additionally a promoter in the form of potassium oxide, rubidium oxide or cesium oxide or a mixture thereof is present on the carrier.

In co-pending U.S. patent application Ser. No. 874,924, filed June 16, 1986, now U.S. Pat. No. 4,701,437, is described a process for the preparation of a silver-containing catalyst suitable for the oxidation of ethylene to ethylene oxide, whereby a silver compound and, if desired, a promoter are applied to a carrier, after which the silver compound is reduced to metallic silver, and in which process the carrier has been prepared by mixing an aluminum compound with a tin compound and by calcining the obtained mixture. The catalyst has a high activity.

There has now been found that a silver catalyst may be prepared with a high activity, a high selectivity and a very high stability by the process of the instant invention.

SUMMARY OF THE INVENTION

The invention relates to a process for the preparation of a silver-containing catalyst suitable for the oxidation of ethylene to ethylene oxide which comprises (a) mixing alumina with a tin compound and with an alkali metal compound,
(b) calcining the mixture to obtain an alkali-enriched and tin-containing alumina carrier,
(c) applying a silver compound to the alumina carrier and converting said silver compound to metallic silver.

DESCRIPTION OF THE PREFERRED EMBODIMENTS

The process according to the invention differs from the process according to co-pending U.S. patent application Ser. No. 874,924, now U.S. Pat. No. 4,701,437, in that an alkali metal compound has been added additionally in the preparation of the alumina carrier.

The aluminum oxides can be several modifications of aluminum oxide, such as gamma-aluminum oxide, which when calcined at a temperature between 1200° C. and 1700° C. generally produce alpha-aluminum oxide. Another possibility is to choose a hydrated aluminum oxide, such as boehmite, which via gamma-aluminum oxide produces alpha-aluminum oxide.

The alkali metal compounds, used for mixing with the aluminum oxide carrier and the tin compound, comprise alkali metal hydroxides and alkali metal salts, such as fluorides, nitrates, chlorides or sulphates. Preferably potassium, rubidium or cesium compounds are used, most preferably cesium compounds, e.g. cesium chloride, cesium fluoride or cesium sulphate.

The quantity of alkali metal compound that is mixed with the alumina is chosen in such an amount, that the atom ratio of the alkali metal/aluminum is between 0.0001 and 0.1, preferably between 0.001 and 0.01.

Examples of tin compounds are tin salts, such as stannic chloride, stannic bromide, stannic fluoride, stannic iodide, stannic nitrate, stannic sulphate, stannic tartrate, stannic chromate. Salts of divalent tin may be suitable as well, e.g. stannous sulphate. Stannic sulphate and stannous sulphate are the most preferred.

The quantity of tin compound that is mixed with the alumina is chosen in such an amount, that the atom ratio of the tin/aluminum is between 0.001 and 0.1, preferably between 0.005 and 0.05.

It has been found that the Sn/Al atom ratio and the Cs/Al atom ratio at the surface of the carrier is greater than the weighed-out Sn/Al and Cs/Al atom ratios respectively. It has further been found that the tin particles at the surface of the carrier have a great influence of the distribution of the metallic silver over the surface, after impregnation of the carrier with the silver compounds and subsequent reduction.

Scanning electron microscopy revealed that the silver particles on the carrier surface were invisible and could not be detected apartly, which is in contrast to silver particles of a commercial catalyst, which particles could be seen and had a diameter of about 0.2-0.5 $\mu$m. One could also speak of a silver mirror on the surface of the carrier in the catalyst according to the invention.

For the preparation of the alkali metal-enriched and tin modified alpha-alumina carrier, preferably alumina is mixed with water, the tin compound and the alkali metal compound, and the resulting mixture is extruded to shaped carrier particles, which latter are calcined. The calcination can take place in one or more steps, depending on the choice of starting material. In general, sufficient water is added to make the mixture extrudable. The extrudable paste obtained is then extruded in an extruder to form shaped pieces. These shaped pices are heated, during which water still present is evaporated. The solid pieces are then calcined. In order to prepare the alpha aluminum oxide modification, calcination up to a temperature of between 1200° C. and 1700° C. is necessary. Suitable starting materials are powders of gamma-aluminum oxide, alpha-aluminum oxide monohydrate, alpha-aluminum oxide trihydrate and beta-aluminum oxide monohydrate, which are sintered during the calcination, with fusion of the powder particles taking place. The heating and calcination also changes the crystal structure: the cubic structure of gamma aluminum oxide changes into the hexagonal structure of alpha aluminum oxide.

The effective catalyst surface area can vary from between 0.1 and 5 $m^2/g$, preferably between 0.2 and 2 $m^2/g$. It has also been found that for the alpha-aluminum oxide, the alkali metal (e.g., cesium) is present at the surface at a concentration higher than is to be expected on the basis of the weighed-out quantity of alkali metal.

In order to prepare the catalyst, the alkali enriched and tin modified alumina carrier is impregnated with a solution of a silver compound, sufficient to apply, as wished, 1 to 25 weight percent of silver, calculated on the weight of the total catalyst, on the carrier. The impregnated carrier is separated from the solution, if necessary and the precipitated silver compound is reduced to metallic silver. It may be that the whole solution is impregnated on the carrier.

Preferably, a promoter is added, for example one or more of the alkali metals: potassium, rubidium or cesium. The promoters can be applied on the carrier before, during or after the impregnation with the silver compound. The promoter can also be applied on the carrier after the silver compound has been reduced to silver.

In general, the carrier is mixed with an aqueous solution of a silver salt or a silver complex, so that the carrier is impregnated with this solution, after which the carrier may be separated from the solution if necessary and subsequently dried. The impregnated carrier is then heated to a temperature of between 100° C. and 400° C. for a period necessary for the silver salt (or complex) to decompose and form a finely distributed layer of metallic silver which adheres to the inner and outer surfaces. Temperatures above 400° C. should be avoided, since then sintering of the silver particles takes place.

Various methods are known for adding the silver. The carrier can be impregnated with an aqueous solution of silver nitrate, then dried, after which the silver nitrate is reduced with hydrogen or hydrazine. The carrier can also be impregnated with an ammonical solution of silver oxalate or silver carbonate, the deposition of silver metal being effected by thermally decomposing the salt. Special solutions of silver salt with certain solubilizing and reducing agents, such as combinations of vicinal alkanolamines, alkyldiamines and ammonia also serve the purpose.

The quantity of added promoter is generally between 20 and 1000 parts by weight of an alkali metal, such as potassium, rubidium or cesium (as metal) per million parts by weight of total catalyst. 50 to 300 parts by weight of alkali metal is particularly suitable. Suitable compounds to serve as starting material for promoters are, for example, nitrates, oxalates, carboxylic acid salts or hydroxides. The most preferred promoter is cesium.

Some excellent methods are known for adding the alkali metals in which these metals can be applied at the same time as the silver. Suitable alkali metal salts are generally salts which are soluble in the silver-depositing liquid phase. Besides the above-mentioned salts, it is also worth mentioning nitrates chlorides, iodides, bromides, bicarbonates, acetates, tartrates, lactates and isopropoxides. The use of alkali metal salts which react with the silver present in the solution and thus cause silver salts to be prematurely precipitated from an impregnating solution should, however, be avoided. For example, potassium chloride should not be used for impregnating techniques in which an aqueous silver nitrate solution is used, but potassium nitrate can be used instead. Potassium chloride can be suitably used in a process in which an aqueous solution of silver amine complexes, from which no silver chloride will precipitate, is used.

In addition, the amount of alkali metal deposited on the carrier can be adjusted within certain limits by washing out a part of the alkali metal with, preferably, anhydrous methanol or ethanol. This method is employed subsequently if the concentration of the applied alkali metal is found to be too high. The temperatures, contact times and the drying with gases can be adjusted. Care should be taken to ensure that no traces of alcohol remain in the carrier. High temperature heat treatments can also be utilized to remove or otherwise inactivate a portion of the alkali metal deposited on the surface of the carrier.

A preferably employed process consists of the carrier being impregnated with an aqueous solution containing both alkali metal salt and silver salt, the impregnating solution being composed of a silver salt of a carboxylic acid, an organic amine, a salt of potassium, rubidium or cesium and an aqueous solvent. For example, a potassium-containing silver oxalate solution can be prepared in two ways. Silver oxide can be reacted with a mixture of ethylene diamine and oxalic acid, giving a solution containing a silver oxalate ethylene diamine complex, to which a certain amount of potassium and possibly other amines such as ethanolamine is added. Silver oxalate can also be precipitated from a solution of potassium oxalate and silver nitrate, the silver oxalate thus obtained then being repeatedly washed in order to remove the attached potassium salts until the desired potassium content is obtained. The potassium-containing silver oxalate is then solubilized with ammonia and/or amine. Solutions containing rubidium and cesium can also be prepared in this way. The thus impregnated carriers are then heated to a temperature of between 100° C. and 400° C., preferably between 125° C. and 325° C.

It should be noted that, irrespective of the nature of the silver in the solution before the precipitation onto the carrier, reference is always made to reduction to metallic silver, whereas it could also be referred to as decomposition on heating. It is preferred to think in terms of reduction, since positively charged Ag ions are converted into metallic Ag. The reduction times can be simply adapted to the starting materials employed.

As mentioned above, a promoter is preferably added to the silver. Cesium is the most preferred promoter in view of the fact that its selectivity for ethylene oxide has been found to be the highest in comparison with the use of potassium or rubidium as promoter.

In a particularly preferred process the instant invention comprises a process for the preparation of a silver-containing catalyst suitable for the oxidation of ethylene to ethylene oxide which comprises
  (a) mixing an alumina selected from the group consisting of anhydrous alumina, hydrated alumina and mixtures thereof with water and with a tin-compound selected from stannous sulfate, stannic sulfate and mixtures thereof and with a cesium salt of hydroxide,
  (b) extruding the resultant mixture,
  (c) calcining the extruded mixture at a temperature between about 1200° C. and about 1700° C. to prepare a carrier,
  (d) impregnating the carrier with a solution of a silver salt or complex sufficient to apply from about 1 to about 25 percent by weight of silver, calculated on the weight of the total catalyst on the carrier surface,
  (e) impregnating the carrier, prior to, simultaneously with or subsequent to step (d) with a solution of one or more compounds of the alkali metals potassium, rubidium or cesium sufficient to apply to the carrier from about 20 to about 1000 parts by weight of the alkali metal (measured as the metal) per million parts by weight of the total catalyst, and (f) reducing the impregnated silver salt or complex to metallic silver.

The silver catalysts prepared by the process according to the present invention appear to be particularly stable catalysts for the direct catalytic oxidation of ethylene to ethylene oxide with the aid of molecular oxygen. The conditions for carrying out the oxidation reaction in the presence of the silver catalysts according to the invention are fairly similar to those already described in the literature. This applies to, for example, suitable temperatures, pressures, residence times, diluents such as nitrogen, carbon dioxide, steam, argon, ethane or other saturated hydrocarbons, the presence or absence of moderating agents to control the catalytic action, for example 1,2-dichloroethane, vinyl chloride or chlorinated polyphenyl compounds, the desirability of employing either recirculating treatments or successive conversions in different reactors to enhance the yield of ethylene oxide, as well as any other special conditions which may be chosen for processes for the preparation of ethylene oxide. Usually, the pressures employed vary from about atmospheric pressure to about 35 bar. Higher pressures are, however, by no means excluded. The molecular oxygen employed as reactant can be obtained from conventional sources. The oxygen feed can consist of substantially pure oxygen, of a concentrated oxygen stream consisting of a large amount of oxygen with smaller amounts of one or more diluents, such as nitrogen, argon, etc., or of another oxygen-containing stream, such as air.

In a preferably employed application of the silver catalysts according to the present invention, ethylene oxide is prepared by contacting an oxygen-containing gas that has been separated from air and that contains not less than 95% oxygen with ethylene in the presence of the catalysts in question at a temperature within the range of 210° C. to 285° C. and preferably between 225° C. and 270° C.

The ranges and limitations provided in the instant specification and claims are those which are believed to particularly point out and distinctly claim the instant invention. It is, however, understood that other ranges and limitations that perform substantially the same function in substantially the same manner to obtain the same result are intended to be within the scope of the instant invention as defined by the instant specification and claims.

In the reaction of ethylene with oxygen to ethylene oxide, the ethylene is present in at least a double molecular quantity, but the quantity of ethylene employed is often much higher. The conversion is therefore calculated according to the quantity of converted oxygen in the reaction and we therefore speak of oxygen conversion. This oxygen conversion is dependent on the temperature of the reaction and is a measure of the activity of the catalyst. The values $T_{30}$, $T_{40}$ and $T_{50}$ refer to the temperatures at 30 mol%, 40 mol% and 50 mol% conversion respectively of the oxygen in the reactor. The temperatures are generally higher for a higher conversion and are highly dependent on the catalyst employed and the reaction conditions. In addition to these T-values, one also comes across selectivity values, which indicate the molar percentage of ethylene oxide in the reaction mixture obtained. The selectivity is indicated as $S_{30}$, $S_{40}$ or $S_{50}$, which refers to the selectivity at 30%, 40% or 50% oxygen conversion respectively.

The concept "stability of a catalyst" cannot be expressed directly. Stability measurements require trials of long duration. For measuring the stability, the applicant has a number of tests which are carried out under extreme conditions with space velocities of 30,000 (liter gas) (liter catalyst)$^{-}$h$^{-}$, where liters of throughout gas are understood to be liters STP (standard temperature and pressure). This space velocity is many times higher than the space velocity in commercial processes, which may range from 2800 to 8000 h$^{-}$. The test is carried out for at least 1 month. The abovementioned T- and S-values are measured during the entire period of the test. After the test has been broken off, the total quantity of ethylene oxide per ml catalyst is determined. The difference in selectivity and activity is calculated for a catalyst which would have produced 1000 grams of ethylene oxide per ml catalyst. A new catalyst is considered to be more stable than a known catalyst if the differences in the T- and S-values of the new catalyst are less than those of the standard catalyst which is present during each test. The stability tests are carried out at 35% oxygen conversion.

EXAMPLE 4.21 g stannous sulphate and 0.89 g cesium fluoride dissolved in 150 ml water was mixed with 132.3 g Kaiser aluminum oxide (Al$_2$O$_3$.H$_2$O) by adding the stannous sulpate-cesium fluoride aqueous solution to the aluminum oxide during 1 min, and the mixture was kneaded for 10 min in a masticator and extruded. The resulting shaped pieces were dried for 12 hours at 120° C. and subsequently calcined at progressively higher temperatures. Calcination was started with the temperature rising at a rate of 200° C./h to 500° C. Calcination was continued for 1 hour at 500° C., after which the temperature was raised in 2 hours to 1500° C. and continued for 1 hour at 1500° C. The pore volume of the shaped aluminum oxide pieces was 0.41 ml/g$^{-1}$ and the average pore diameter was 1.66 μm. The weighed-out cesium/aluminum atom ratio was 0.003, the weighed-out tin/aluminum atom ratio was 0.01. X-ray photoelectron spectroscopy of the carrier surface revealed that there the cesium/aluminum atom ratio was 0.042 and the tin/aluminum atom ratio 0.034.

The resulting shaped pieces were impregnated with an aqueous solution of silver oxalate, to which cesium hydroxide was added. The impregnation was carried out for 10 min under vacuum, after which the shaped pieces were separated from the solution and placed in a hot air stream at a temperature of 250°–270° C. for 10 min in order to convert the silver salt to metallic silver. The aqueous solution of silver oxalate was a 28 %wt Ag-containing aqueous solution in which the silver oxalate was complexed with ethylene diamine and to which solution cesium hydroxide had been added. After the hot air treatment the thus impregnated shaped pieces contained 15.5 %wt Ag (calculated on total catalyst weight) and 310 ppm of (impregnated) cesium on the total catalyst weight.

The silver catalyst obtained by the above-described method was then tested. A cylindrical steel reactor with a length of 15 cm and a diameter of 3 mm was filled entirely with catalyst particles of about 0.3 mm in size. The reactor was placed in a bath in which silicon/aluminum particles were present in a fluidized state. A gas mixture with the following composition was passed through the reactor: 30 ml% ethylene, 8.5 mol% oxygen, 7 mol% carbon dioxide and 54.5 mol% nitrogen and 7 parts per million parts of gas of vinyl chloride as moderator. The space velocity was 30,000 1l−h−. The pressure was 15 bar and the temperature was dependent on the set oxygen conversion. The measuring equipment was connected to the reactor and to a computer. The conversion and the temperature could be accurately controlled. The concentrations of the reaction components were determined with the aid of gas chromatography. The stability test was carried out at an oxygen conversion of 35%.

The reaction temperature at 35% oxygen conversion was determined during the entire duration of the test. The selectivity in respect of ethylene oxide was also determined. After 30 days the total quantity of ethylene oxide produced per ml catalyst was determined. From the measured reaction temperatures, starting at the beginning of the reaction, the temperature rise in °C. was calculated for the moment at which 1000 g ethylene oxide per ml catalyst would have been produced ($\Delta T_{35}^{1000}$). From the measured selectivities, starting at the beginning of the reaction, the selectivity decrease in %mol was calculated for the moment at which 1000 g ethylene oxide per ml catalyst would have been produced ($\Delta S_{35}^{1000}$). The same measurements and calculations were carried out for a standard catalyst in the test (Shell S839 commercial catalyst).

The table gives the relative value of the $\Delta S_{35}^{1000}$ and $\Delta T_{35}^{1000}$, expressed in a percentage of the $\Delta S_{35}^{1000}$- and $\Delta T_{35}^{1000}$-values of the standard silver catalyst, that is, $\Delta S_{35}^{1000}$ for example 1 is divided by $\Delta S_{35}^{1000}$ for the standard catalyst times 100% to provide the percentage value.

TABLE

| Example | Catalyst % wt Ag | ppm cesium | $\Delta S_{35}^{1000}$ (rel.) % | $\Delta T_{35}^{1000}$ (rel.) % |
|---|---|---|---|---|
| 1 | 15.5 | 310 | 20 | 20 |
| Comparison | Standard commercial catalyst | | 100 | 100 |

It is observed that the silver particles on the standard commercial catalyst after 30 days of operation under the severe conditions, had already sintered with each other, while the silver on the catalyst made by the process according to our invention showed no signs of sintering after the same time of operation under the severe conditions. Consequently the catalyst according to the invention has a much greater stability than the standard catalyst.

Actually the catalyst according to the invention showed a selectivity loss of 0.7% (to ethylene oxide) and an activity loss in terms of increase in reaction temperature of 2° C.

The catalyst according to the invention had an $S_{40}$-value and a $T_{40}$-value of 79.6% and 230° C. respectively (measured on the catalyst under normal working conditions with GHSV of 3300 h−1).

I claim:

1. A process for the preparation of a silver-containing cataylst suitable for the oxidation of ethylene to ethylene oxide which comprises
   (a) mixing alumina with water, a tin compound and with an alkali metal compound,
   (b) calcining the mixture to obtain an alkali-enriched and tin-containing alumina carrier,
   (c) applying a solution of a silver compound to the alumina carrier and converting said silver compound to metallic silver.

2. The process as claimed in claim 1, wherein the alumina is anhydrous or hydrated alumina.

3. The process as claimed in claim 2, wherein the alkali metal compound is a salt or a hydroxide of the alkali metal.

4. The process as claimed in claim 3, wherein the alkali metal salt is a fluoride, nitrate, chloride or a sulphate.

5. The process as claimed in claim 4, wherein the alkali metal is cesium.

6. The process as claimed in claim 1, wherein the tin compound is a tin salt.

7. The process as claimed in claim 6, wherein the tin salt is stannous sulphate or stannic sulphate.

8. The process as claimed in claim 1, wherein the calcination under (b) is carried out at a temperature of between 1200° C. and 1700° C.

9. The process as claimed in claim 1, wherein alumina is mixed with water, the tin compound and the alkali metal compound, the resulting mixture is extruded to shaped carrier particles, which latter are calcined.

10. The process as claimed in any one of the claims 1–9, wherein the calcined alumina carrier is impregnated with a solution of a silver salt or -complex sufficient to apply 1 to 25 percent by weight of silver, calculated on the weight of total catalyst, on the carrier surface, and the precipitated silver salt or -complex is reduced to metallic silver.

11. The process as claimed in claim 10, wherein additionally an alkali promoter is applied simultaneously with the impregnation of the silver.

12. The process as claimed in claim 11, wherein besides the silver salt or -complex a sufficient quantity of one or more compounds of the alkali metals potassium, rubidium or cesium is applied to the carrier to deposit between 20 and 1000 parts by weight of the alkali metal (measured as the metal) per million parts by weight of total catalyst.

13. A catalyst prepared by means of a process as claimed in any one of the claims 1–9, 11 and 12.

14. A process for the preparation of a silver-containing catalyst suitable for the oxidation of ethylene to ethylene oxide which comprises
   (a) mixing an alumina selected from the group consisting of anhydrous alumina, hydrate alumina and mixtures thereof with water and with a tin compound selected from stannous sulfate, stannic sulfate and mixtures thereof and with a cesium salt or hydroxide,
   (b) extruding the resultant mixture,
   (c) calcining the extruded mixture at a temperature between about 1200° C. and about 1700° C. to prepare a carrier,
   (d) impregnating the carrier with a solution of a silver salt or complex sufficient to apply from about 1 to about 25 percent by weight of silver, calculated on the weight of the total catalyst, on the carrier surface,
   (e) impregnating the carrier, prior to, simultaneously with or subsequent to step (d) with a solution of one or more compounds of the alkali metals potassium, rubidium or cesium sufficient to apply to the carrier from about 20 to about 1000 parts by weight of the alkali metal (measured as the metal) per million parts by weight of the total catalyst, and (f) reducing the impregnated silver salt or complex to metallic silver.

15. A silver-containing catalyst suitable for the oxidation of ethylene to ethylene oxide comprising
    (a) from 1 to 25 percent by weight of silver, calculated on the weight of the total catalyst, on the surface of the carrier
    (b) an alkali enriched and tin modified alpha-alumina carrier.

16. The silver containing catalyst as claimed in claim 15, wherein an alkali metal promoter is present on the surface of the carrier.

17. The silver-containing catalyst as claimed in claim 16, wherein between 20 and 1000 parts by weight of potassium, rubidium or cesium (measured as the metal) per million parts by weight of total catalyst is present on the surface of the carrier.

18. The process as claimed in claim 10, wherein additionally an alkali metal promoter is applied non-simultaneously with the impregnation with the silver.

19. The process as claimed in claim 18, wherein besides the silver salt or -complex a sufficient quantity of one or more compounds of the alkali metals potassium, rubidium or cesium is applied to the carrier to deposit between 20 and 1000 parts by weight of the alkali metal (measured as the metal) per million parts by weight of total catalyst.

* * * * *